(12) United States Patent
Clement (10) Patent No.: US 9,750,480 B2
(45) Date of Patent: Sep. 5, 2017

(54) SYSTEMS AND METHODS FOR MEASUREMENT OF TISSUE PERFUSION

(71) Applicant: THE CLEVELAND CLINIC FOUNDATION, Cleveland, OH (US)

(72) Inventor: Gregory T. Clement, Cleveland, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 274 days.

(21) Appl. No.: 14/575,219

(22) Filed: Dec. 18, 2014

(65) Prior Publication Data

US 2015/0173704 A1  Jun. 25, 2015

Related U.S. Application Data

(60) Provisional application No. 61/920,507, filed on Dec. 24, 2013.

(51) Int. Cl.
*A61B 8/00* (2006.01)
*A61B 8/06* (2006.01)
*A61B 8/08* (2006.01)

(52) U.S. Cl.
CPC .............. *A61B 8/06* (2013.01); *A61B 8/481* (2013.01); *A61B 8/5207* (2013.01)

(58) Field of Classification Search
CPC .. A61B 8/00; A61B 8/481; A61B 8/06; A61B 8/543; A61B 8/08
See application file for complete search history.

(56) References Cited

U.S. PATENT DOCUMENTS

| 5,860,931 | A | 1/1999 | Chandler |
| 7,753,850 | B2 | 7/2010 | Averkiou et al. |
| 2006/0079773 | A1* | 4/2006 | Mourad ............... A61B 5/0048 600/438 |
| 2012/0323118 | A1 | 12/2012 | Menon Gopalakrishna et al. |
| 2014/0254909 | A1* | 9/2014 | Carmi ................... A61B 6/032 382/131 |

FOREIGN PATENT DOCUMENTS

WO   2013061202 A2   5/2013

OTHER PUBLICATIONS

Chen et al., "Rapid 3D Imaging of Contrast Flow: Application in a Perfused Kidney Phantom", Ultrasound Med Biol., May 2009, 35(5), pp. 813-828.

(Continued)

*Primary Examiner* — Joel Lamprecht
(74) *Attorney, Agent, or Firm* — Tarolli, Sundheim, Covell & Tummino LLP (57) ABSTRACT

One aspect of the present disclosure relates to a system that can measure profusion through a volume of tissue. The system can include a non-transitory memory that stores instructions and a processor that can be configured to execute the instructions to at least: receive an ultrasound signal response of a contrast agent within a volume of interest and determine the perfusion through the volume of tissue based on a probabilistic constant related to the geometry, the tissue density, the ultrasound signal response, and a feature of the geometry. The ultrasound signal response can include a time dimension and three position dimensions. The volume of interest can include a tissue density and a geometry.

12 Claims, 6 Drawing Sheets

(56) References Cited

OTHER PUBLICATIONS

Foster et al., "Reinforced Walks in Two and Three Dimensions", New Journal of Physics, 11, Feb. 4, 2009, pp. 1-21.
Herzer et al., "Capacitive-Coupled Current Sensing and Auto-Ranging Slope Compensation for Current Mode SMPS with Wide Supply and Frequency Range", IEEE, 2009, pp. 1-4.
Hudson et al., "Quantification of Flow Using Ultrasound and Microbubbles: A Disruption Replenishment Model Based on Physical Principles", Ultrasound in Med. & Biol., 2009, vol. 35, No. 12, pp. 2007-2020.
Kolář et al., "Advanced Methods for Perfusion Analysis in Echocardiography", Physiol. Res. 2010, 59 (Suppl. 1), pp. S33-S41.
Krix et al., "A Multivessel Model Describing Replenishment Kinetics of Ultrasound Contrast Agent for Quantification of Tissue Perfusion", Ultrasound in Med. & Biol., 2003, vol. 29, No. 10, pp. 1421-1430.
Strouthos et al., "Indicator Dilution Models for the Quantification of Microvascular Blood Flow with Bolus Administration of Ultrasound Contrast Agents", IEEE Transactions on Ultrasonics, Ferroelectrics, and Frequency Control, Jun. 2010, vol. 57, No. 6, pp. 1296-1310.
Numata et al., "Contrast Enhanced Ultrasound of Hepatocellular Carcinoma", World Journal of Radiology, Feb. 2010, 25, 2(2), pp. 68-82.
Paltiel et al., "Multi-Planar Dynamic Contrast-Enhanced Ultrasound Assessment of Blood Flow in a Rabbit Model of Testicular Torsion", Ultrasound in Med. & Biol., 2014, vol. 40, No. 2, pp. 361-370.
Quaia, "Assessment of Tissue Perfusion by Contrast-Enhanced Ultrasound", Eur Radiol (2011) 21, pp. 604-615.
Thierman et al., "Automated Sonographic Evaluation of Testicular Perfusion", Phys. Med. Biol. 51, 2006, pp. 3419-3432.
Veronesi et al., "Semi-Automated Analysis of Dynamic Changes in Myocardial Contrast from Real-Time Three-Dimensional Echocardiographic Images as a Basis for Volumetric Quantification of Myocardial Perfusion", European Journal of Echocardiography 10, 2009, pp. 485-490.
Wei et al., "Quantification of Myocardial Blood Flow With Ultrasound-Induced Destruction of Microbubbles Administered as a Constant Venous Infusion", Circulation 97, 1998, pp. 473-483.
Wei et al., "Quantification of Renal Blood Flow with Contrast-Enhanced Ultrasound", Journal of the American College of Cardiology, 2001, vol. 37, No. 4, pp. 1135-1140.

* cited by examiner

SYSTEMS AND METHODS FOR MEASUREMENT OF TISSUE PERFUSION

RELATED APPLICATIONS

This application claims the benefit of U.S. Provisional Application No. 61/920,507, filed Dec. 24, 2013, entitled "SYSTEMS AND METHODS FOR MEASUREMENT OF TISSUE PERFUSION." This provisional application is hereby incorporated by reference in its entirety for all purposes.

TECHNICAL FIELD

The present disclosure relates generally to measurement of tissue profusion and, more specifically, to systems and methods that can non-invasively and quantitatively measure the perfusion through a volume of tissue within a patient's body in real-time.

BACKGROUND

Contrast-enhanced ultrasound ("CEUS") imaging can be used to observe perfusion according to different techniques, but many of these techniques can produce only relative observations. These techniques often collect dynamic data over a single tissue plane, so that the results are highly dependent on the orientation of the ultrasound probe and the results for the single tissue plane do not accurately reflect global perfusion (e.g., of an organ). Other techniques that map perfusion over a volume are accurate under controlled conditions, but are application limited due to a lack of an analytic approach that is valid and accurate in three dimensions.

SUMMARY

The present disclosure relates generally to measurement of tissue profusion and, more specifically, to systems and methods that can non-invasively and quantitatively measure the perfusion through a volume of tissue within a patient's body in real-time. Unlike previous solutions, the systems and methods provide an analytic approach that is valid and accurate in three dimensions without depending on the orientation of the ultrasound ("US") probe.

In one aspect, the present disclosure can include a system that can quantitatively measure perfusion through a volume of tissue. The system includes a memory to store computer-executable instructions. The system also includes a processor that executes the computer-executable instructions to at least: receive an ultrasound signal response, with a time dimension and three position dimensions, from a contrast agent within a volume of interest with a unique tissue density and geometry. The perfusion through the volume of tissue is determined based on a probabilistic constant related to the geometry, the tissue density, the ultrasound signal response, and a feature of the geometry.

In another aspect, the present disclosure can include a method for quantitatively measuring perfusion through a volume of tissue. One or more acts of the method can be represented by computer-executable instructions that can be executed by a system comprising a processor. The acts can include: receiving an ultrasound signal response comprising a time dimension and three tissue position dimensions from a contrast agent within a volume of interest, wherein the volume of interest comprises a tissue density and a geometry; determining a probabilistic constant related to the geometry; determining a ratio of mean velocity and mean path length based on the ultrasound signal response; and determining the perfusion through the volume of tissue based on the probabilistic constant and the ratio.

In a further aspect, the present disclosure can include a computer-readable medium having stored thereon instructions that, upon execution, cause a processor of one or more computing devices to perform operations for quantitatively measuring perfusion through a volume of tissue. The operations can include: receiving an ultrasound signal response comprising a time dimension and three tissue position dimensions from a contrast agent within a volume of interest, wherein the volume of interest comprises a tissue density and a geometry; determining a probabilistic constant related to the geometry; determining a ratio of mean velocity and mean path length based on the ultrasound signal response; and determining the perfusion through the volume of tissue based on the probabilistic constant and the ratio.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

In the context of the present disclosure, the singular forms "a," "an" and "the" can also include the plural forms, unless the context clearly indicates otherwise. The terms "comprises" and/or "comprising," as used herein, can specify the presence of stated features, steps, operations, elements, and/or components, but do not preclude the presence or addition of one or more other features, steps, operations, elements, components, and/or groups. As used herein, the term "and/or" can include any and all combinations of one or more of the associated listed items. Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "ultrasound" imaging can refer to a medical imaging modality that employs sound waves (e.g., with a frequency greater than or equal to 20,000 Hz) to produce real-time images (or "sonograms") of an internal structure of a patient's body. In some instances, the internal structure of the patient's body can be opaque to light. The terms "ultrasound imaging", "sonography", and "acoustic imaging" can be used interchangeably herein.

As used herein, the term "three-dimensional" ultrasound can refer to an ultrasound image that is valid and accurate in three dimensions. An example of a three-dimensional ultrasound modality can include contrast-enhanced ultrasound ("CEUS") imaging.

As used herein, the term ultrasound "contrast agent" can relate to chemical or molecule with different echogenicities that the soft tissue of the body to enhance the echo of sound waves, producing an ultrasound image (or "sonogram") with an increased contrast compared to an ultrasound image produced from the ultrasound alone. An example of an ultrasound contrast agent can include a plurality of gas-filled microbubbles, each having a higher echogenicity that is higher than an echogenicity of soft tissue in the volume of tissue.

As used herein, the term "perfusion" can refer to a passage of a fluid through a volume of tissue. In some instances, the fluid can pass through one or more vessels associated with a volume of tissue. In these instances, the fluid can be blood and the vessels can be a capillary bed.

As used herein, the term "quantitative measure" can refer to a numerical measurement, but does not exclude other measurements, including qualitative observational measurements.

As used herein, the terms "subject" and "patient" can refer, interchangeably, to any warm-blooded organism including, but not limited to, a human being, a pig, a rat, a mouse, a dog, a cat, a goat, a sheep, a horse, a monkey, an ape, a rabbit, a cow, etc. The terms "subject" and "user" can be used interchangeably herein.

II. Overview

The present disclosure relates generally to measurement of tissue profusion and, more specifically, to systems and methods that can non-invasively and quantitatively measure the perfusion through a volume of tissue within a patient's body in real-time. Unlike previous solutions, the systems and methods provide an analytic approach that is valid and accurate in three dimensions without depending on the orientation of the ultrasound probe.

In some instances, the systems and methods can achieve the quantitative measure of perfusion by a non-invasive three-dimensional imaging modality in connection with an approach for analyzing a time-dependent signal from the three-dimensional imaging modality, such as three-dimensional contrast-enhanced ultrasound ("CEUS") imaging. CEUS can apply one or more ultrasound contrast agents apply one or more contrast agents to enhance the echo of sound waves to produce a sonogram with an increased contrast compared to a sonogram produced from ultrasound alone. Based on the contrast-enhanced image, the systems and methods can determine the quantitative measure of profusion.

The quantitative measurement of perfusion can be used, for example, to determine a health status of the tissue and/or to identify an abnormality within the tissue. As an example, the quantitative measurement can be used to diagnose abnormal kidney function, brain function, testicle function, liver function, and the like. According to another example, the quantitative measurement can be used to detect the presence of hyper-perusing or hypo-perusing tumors. In another example, the quantitative measurements can be used as a tool for detecting ablated tissues that can serve to guide ablative image guided therapies.

III. Systems

One aspect of the present disclosure can include a system that can that quantitatively measure perfusion through a volume of tissue within a patient's body. The system can utilize a non-transitory memory to store computer-executable instructions and a processor that executes the computer-executable instructions. Upon execution, the instructions can cause one or more computing devices to at least: receive an ultrasound signal response of a contrast agent within a volume of interest, wherein the ultrasound signal response comprises a time dimension and three position dimensions, and wherein the volume of interest comprises a tissue density and a geometry; and determine the perfusion through the volume of tissue based on a probabilistic constant related to the geometry, the tissue density, the ultrasound signal response, and a feature of the geometry.

Figure 1:
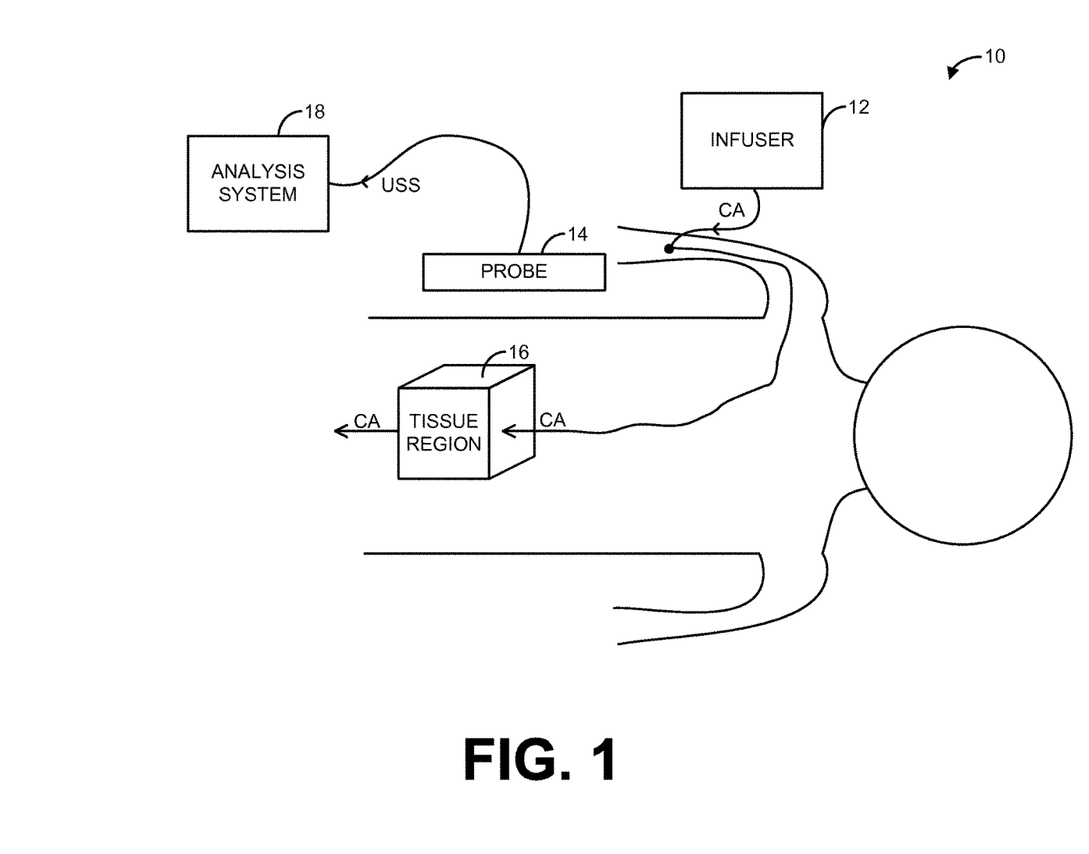
FIG. 1 is a schematic block diagram depicting a system that determines perfusion through a volumetric tissue region in a patient's body based on an ultrasound signal response concurrent with an infusion of an ultrasound contrast agent in accordance with an aspect of the present disclosure.

As shown in FIG. 1, one aspect of the present disclosure can include a system 10 configured to determine the perfusion through a tissue region 16 (e.g., a volumetric tissue region) in a patient's body based on an ultrasound signal response (USS) concurrent with an infusion of an ultrasound contrast agent (CA). System 10 can include an infuser 12 that can deliver the ultrasound contrast agent (CA) to the patient, a probe 14 that can detect the ultrasound signal response (USS) of the ultrasound contrast agent (CA) within the tissue region 16 over time, and an analysis system 18 that can determine the perfusion through the tissue region 16 based on the ultrasound signal response (USS).

The infuser 12 can deliver the ultrasound contrast agent (CA) to the patient. The ultrasound contrast agent (CA) can exhibit a different echogenicities than soft tissue of the tissue region 16. An example ultrasound contrast agent can include a plurality of gas-filled microbubbles with each of the plurality of gas-filled microbubbles having an echogenicity that is higher than an echogenicity of soft tissue in the tissue region 16.

The infuser 12 can be coupled to an intravenous access device and a reservoir that stores the ultrasound contrast agent (CA). The reservoir can store an amount of ultrasound contrast agent (CA) sufficient to provide the ultrasound contrast agent (CA) to the tissue region 16 at a predefined rate for a time. The reservoir can be coupled to a vascular access device that can facilitate delivery into a patient's vasculature. An example of a vascular access device is an "intravenous access device," a device that can facilitate delivery of the ultrasound contrast agent (CA) to a peripheral vein. Example intravenous access devices include, but are not limited to, a catheter, a disposable intravenous tube, a needle and/or a valve. The infuser 12 can include a processor and/or a non-transitory memory that can allow the infuser 12 to regulate the delivery of the ultrasound contrast agent (CA) to the peripheral vein. For example, the processor and/or the non-transitory memory can ensure that the infuser 12 delivers the ultrasound contrast agent (CA) to the peripheral vein at a predefined controlled rate and/or a constant rate. According to an example, the infuser 12 can provide constant rate of delivery of the ultrasound contrast agent (CA) to the patient's vein, and the constant rate can be controlled to facilitate the analysis system 18 determining the perfusion.

The probe 14 can include a three-dimensional (e.g., providing data in the X-dimension, Y-dimension, and Z-dimension) ultrasound transducer that sends the sound waves at different angles to the tissue region 16 and receives echoes from the ultrasound contrast agent (CA) within the tissue region 16 in return. The ultrasound transducer can convert the sound energy of the echoes to an electrical energy signal that is transmitted to the analysis system 18 as the ultrasound signal response (USS). Although the probe 14 is illustrated as not interfacing with the patient's body, it will be understood that to record the ultrasound signal response (USS), the probe 14 can be located in any position on the surface of the patient's body that can facilitate the creation of an image of the tissue region 16 from the ultrasound tissue response (USS). The probe 14 can directly interface with the patient's body; however, the probe 14 does not need to directly interface with the patient's body. For example, the probe 14 can interface with the patient's body via a material applied to the patient's skin to enhance the sound waves (e.g., a water-based gel), or via a different type of interface.

The analysis system 18 can receive the ultrasound response signal (USS) from the probe 14 at different times while the infuser 12 regulates the infusion of the ultrasound contrast agent (CA) to the tissue region 16. Accordingly, the ultrasound signal response can be a function of time and of the three-dimensions of position (e.g., a function of t, X, Y, Z). The analysis system 18 can create an image of the tissue region 16 from the ultrasound response signal (USS). The image can include a plurality of voxels, or three-dimensional pixels, that are created from the data in the ultrasound signal response (USS).

The analysis system 18 can apply an analytic approach to the time-dependent ultrasound signal response that is valid and accurate in three dimensions to measure the perfusion through the tissue region 16. The measurement of perfusion by the analysis system 18 depends on the shape of the tissue region 16 (hereinafter referred to as the volume of interest ("VOI").

Figure 2:
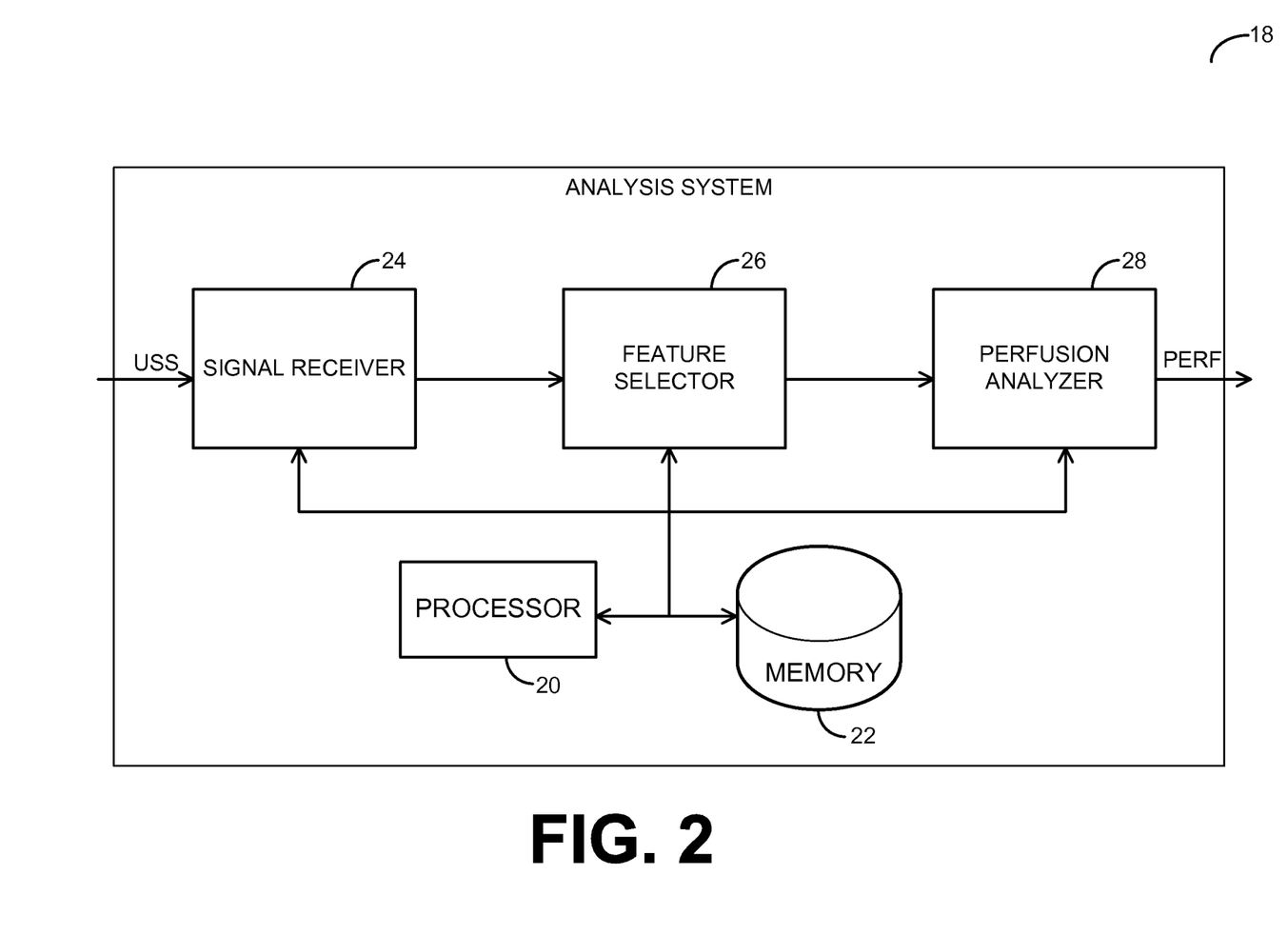
FIG. 2 is a schematic system block diagram depicting the analysis system of FIG. 1 that quantitatively measures perfusion through a volume of interest.

Referring now to FIG. 2, illustrated is an example configuration of the analysis system 18. As illustrated in FIG. 2, the analysis system 18 can include a signal receiver 24, a feature selector 26, and a perfusion analyzer 28 (collectively referred to as "the components"). The components are coupled to a processor 20 and a non-transitory computer-readable memory 22. One or more of the components can be implemented by computer program instructions that can be stored in the non-transitory computer-readable memory 22 (e.g., an electronic, magnetic, optical, electromagnetic, infrared, or semiconductor system, apparatus or device) and provided to the processor 20 (e.g., a processor of a general purpose computer, special purpose computer, and/or other programmable data processing apparatus). The processor 20 can execute the instructions such that a computing device can implement the functions of one or more of the components.

For example, the components 24-28 of FIG. 2 are schematically illustrated as a block diagram with the different blocks representing different components. The functions of one or more of the components can be implemented by computer program instructions. These computer program instructions can be provided to a processor of a general purpose computer, special purpose computer, and/or other programmable data processing apparatus to produce a machine, such that the instructions, which execute via the processor of the computer and/or other programmable data processing apparatus, create a mechanism for implementing the functions of the components specified in the block diagrams.

These computer program instructions can also be stored in a non-transitory computer-readable memory that can direct a computer or other programmable data processing apparatus to function in a particular manner, such that the instructions stored in the non-transitory computer-readable memory produce an article of manufacture including instructions, which implement the function specified in the block diagrams and associated description.

The computer program instructions can also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions of the components specified in the block diagrams and the associated description.

Accordingly, the components described herein can be embodied at least in part in hardware and/or in software (including firmware, resident software, micro-code, etc.). Furthermore, aspects of the components can take the form of a computer program product on a computer-usable or computer-readable storage medium having computer-usable or computer-readable program code embodied in the medium for use by or in connection with an instruction execution system. A computer-usable or computer-readable medium can be any non-transitory medium that is not a transitory signal and can contain or store the program for use by or in connection with the instruction or execution of a system, apparatus, or device. The computer-usable or computer-readable medium can be, for example but not limited to, an electronic, magnetic, optical, electromagnetic, infrared, or semiconductor system, apparatus or device. More specific examples (a non-exhaustive list) of the computer-readable medium can include the following: a portable computer diskette; a random access memory; a read-only memory; an erasable programmable read-only memory (or Flash memory); and a portable compact disc read-only memory.

As described above, the components of the analysis system 18 can include a signal receiver 24, a feature selector 26, and a perfusion analyzer 28. The signal receiver 24 can receive the ultrasound signal response (USS) from the probe 14 at different times. The ultrasound signal response (USS) is a recording of responses from the ULTRASOUND contrast agent (CA) within the tissue region 16 that corresponds to the tissue region 16 (considered a volume of interest (VOI) for analysis purposes). The signal receiver 24 can translate the ultrasound signal response (USS) received at different times to the ULTRASOUND image that exhibits different intensities corresponding to the different voxels. While the signal receiver 24 can be an independent component, the signal receiver 24 can be coupled to the feature selector 26 and/or the perfusion analyzer 28.

The feature selector 26 can determine features unique to the VOI based on the geometry of the VOI and/or the ultrasound signal response. The features determined by the feature selector 26 can be used in the determination of perfusion (PERF) by the perfusion analyzer 28. The feature selector 26 can determine constants based on the geometry of the VOI ($\alpha_\gamma$) and based on the ultrasound signal response (R) that the perfusion analyzer 28 can use in the determination of the perfusion (e.g., PERF is a function of $\alpha_\gamma$ and R).

The probabilistic constant ($\alpha_\gamma$) can be determined completely from the geometry and/or a feature of the geometry without knowledge of the mean path length through the VOI (<L>), which is generally unknown. The feature selector 26 can determine the geometry of the VOI and one or more features corresponding to the geometry of the VOI. In an example, the geometry of the VOI can be a rectangular prism, and the feature selector 26 can determine at least one of the lengths (X), the width (Y), and the height (Z) parameters of the rectangular prism. The feature selector 26 can also determine the probabilistic constant ($\alpha_\gamma$) based on the geometry (and/or a feature of the geometry) and a scale of the volume of interest, which are known.

The feature selector 26 can also determine the ratio (R) of mean velocity (<v>) and the mean path length (<L>) based on the ULTRASOUND signal response. The mean velocity (<v>) and the mean path length (<L>) are both quantities that are generally unknown. The ratio (R) can be determined by the feature selector 26 based on a signal analysis of the ultrasound signal response (USS).

Figure 3:
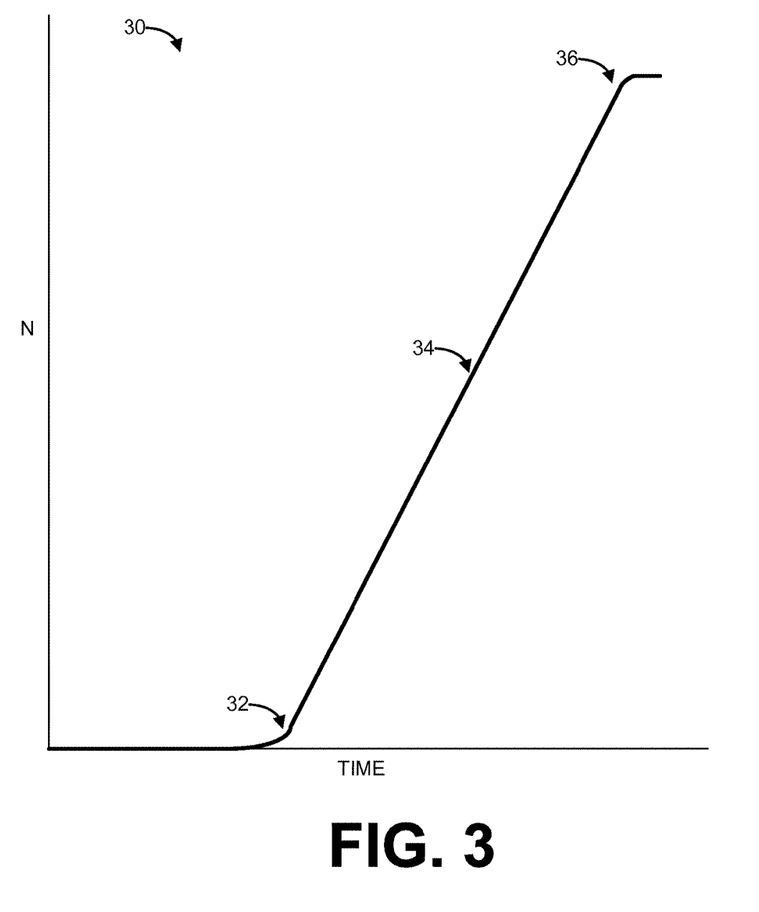
FIG. 3 is a schematic example plot that can be used to determine the ratio (R) of mean velocity and mean path length by the analysis system of FIG. 1.

The ultrasound signal response (USS) can include a time history of intensity values of ultrasound responses of the contrast agent within the VOI. The feature selector 26 can utilize a plot of the number of contrast agent bubbles (N) versus time (TIME) similar to the plot 30 in FIG. 3 to determine the ratio (R). In FIG. 3, element 32 represents the period of time when bubbles first flow into the VOI; element 34 represents the period of time when the signal is increasing linearly (transitory filling stage); and element 36 represents the period of time when the signal is at steady state.

The feature selector 26 can determine the ratio (R) by taking a ratio of the first derivative with respect to time of the signal over the time period where the signal is increasing linearly (e.g., element 34) and the second derivative with respect to time of the signal over a period when the bubbles first flow into the VOI (e.g., element 32). Alternatively, the feature selector 26 can determine the ratio (R) by taking a ratio of the signal over the steady state time period (e.g., element 36) and the first derivative with respect to time of the signal over the time period where the signal is increasing linearly (e.g., element 34).

Referring again to FIG. 2, the feature selector 26 can determine additional features of the VOI that the perfusion analyzer 28 can utilize in the determination of the perfusion. The VOI generally contains one or more tissue types within the tissue region 16. The feature selector 26 can determine a tissue density ($\rho_{tissue}$) of the tissue region 16 corresponding to the VOI. In an example, the tissue density ($\rho_{tissue}$) for a certain tissue region can be constant between different patients, but variable over different tissue regions, so the feature selector 26 can retrieve the tissue density ($\rho_{tissue}$) value from a stored database of tissue density ($\rho_{tissue}$) values for different tissue regions. The perfusion analyzer 28 can determine the perfusion through the VOI further based on the tissue density ($\rho_{tissue}$). The perfusion analyzer 28 can also incorporate one or more features of the geometry in the determination of the perfusion through the VOI.

For example, if the VOI is a rectangular prism, the perfusion analyzer 28 can determine the mean perfusion through the volume of interest corresponding to the tissue region 16 (<Q>) according to the following equation:

$$\langle Q \rangle = \frac{6\alpha_\gamma R}{\rho_{tissue} XY},$$

where $\alpha_\gamma$ represents the probabilistic constant, R represents a ratio of mean velocity and mean path length determined based on the ultrasound signal response, $\rho_{tissue}$ represents the tissue density, and X and Y represent parameters of the feature of the geometry. A full derivation of the mean perfusion (<Q>) is shown in Appendix A.

The mean perfusion (<Q>) depends significantly on the geometry of the VOI. Two volumes in the same region can record different responses due the differences arising solely from probabilistic considerations. To remove these differences, the perfusion analyzer 28 can calibrate the mean perfusion (<Q>) to achieve an absolute measure of perfusion (PERF).

The signal receiver 24 and/or the perfusion analyzer 28 can retrieve the voxels from the surface of the VOI from the ultrasound image. Each of the voxels corresponds to a signal intensity. Each of the signal intensities within the plurality of voxels are related to each other by equations of continuity based on the ultrasound signal response. For example, within the ultrasound image, each voxel can exhibit an intensity value within the ultrasound signal response based on the contrast agent present in the voxel, which is related to the relative quantity of blood within the pixel.

Figure 4:
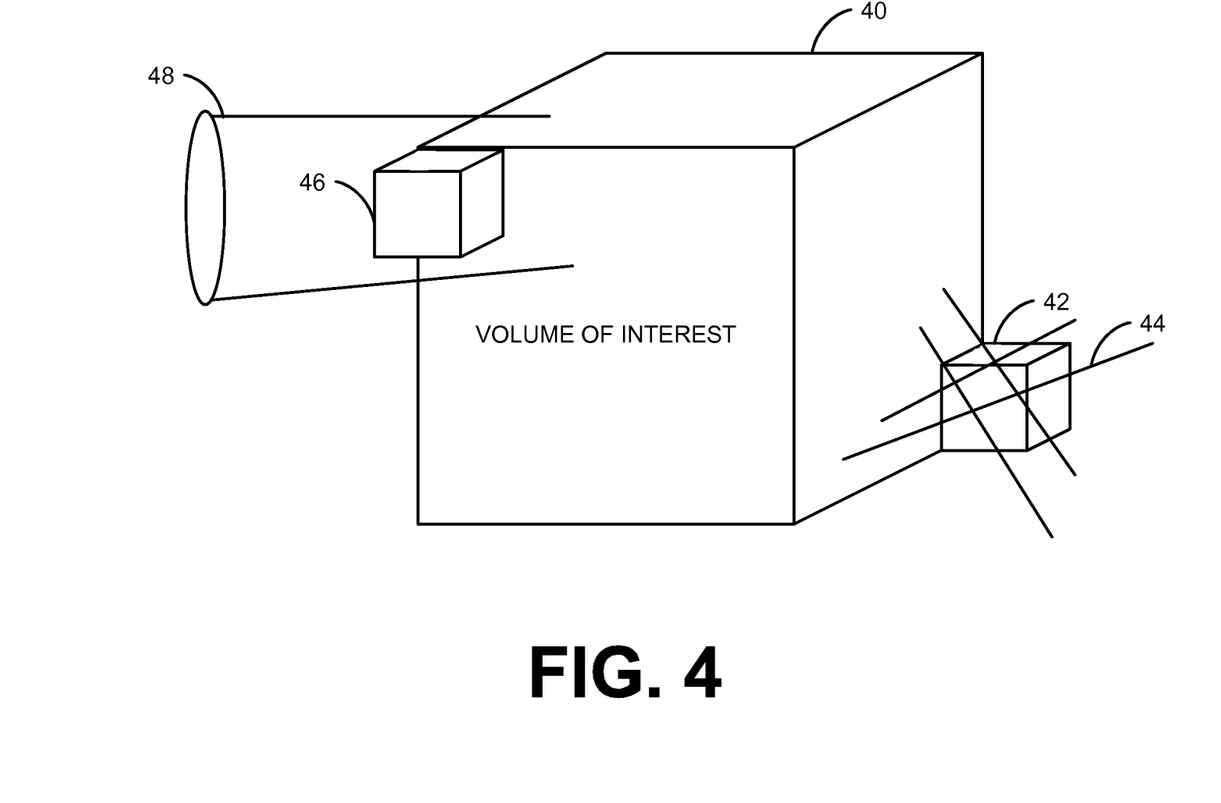
FIG. 4 is a schematic diagram depicting an example of a calibration of voxels of the ultrasound signal with respect to a concentration of blood through the voxels that can be calculated by the analysis system of FIG. 1.

FIG. 4 is a schematic illustration of a volume of interest 40 with two example voxels 42, 46 on the surface of the volume of interest 40. FIG. 4 shows only two voxels for simplicity of illustration and explanation. However, it will be understood that the surface of the volume of interest 40 is divided into the plurality of voxels of more than two voxels.

In FIG. 4, voxel 42 is less than 100% full of blood vessels 44, while voxel 46 is 100% full of blood from a blood vessel 48 that is bigger than the voxel 46. Accordingly, voxel 46 can exhibit a maximum intensity in the US signal response. The intensity value corresponding to the voxel 46 can be identified and stored in the non-transitory computer-readable memory 22 or in a temporary memory. The intensity of the voxel 42 with less than 100% fill of blood vessels can be normalized with respect to the stored intensity corresponding to the voxel 46 that is entirely within a vessel. The additional voxels on the surface that are not illustrated in FIG. 4 can also be normalized with respect to the stored intensity corresponding to the voxel 46 to achieve a fluid percentage within each of the plurality of voxels. Assuming that 50% of the total fluid percentage flows into the volume of interest and 50% of the total fluid percentage flows out of the volume of interest, such that half of the fluid flied area is used as the surface area of blood input to the volume of interest, the voxels can be calibrated to achieve an absolute measure of perfusion.

IV. Methods

Figure 5:
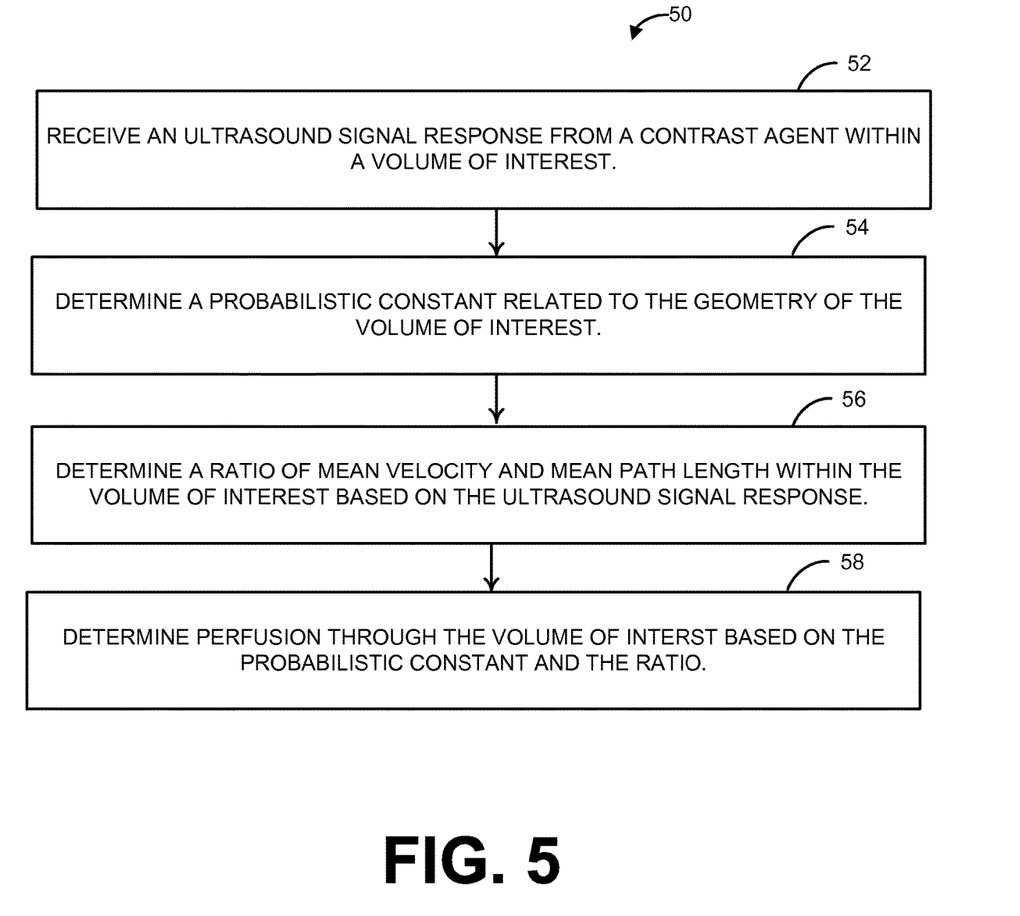
FIG. 5 is a schematic process flow diagram depicting a method for quantitatively measuring perfusion through a volume of interest in accordance with another aspect of the present disclosure.

Another aspect of the present disclosure can include a method for quantitatively measuring perfusion through a volume of interest, according to an aspect of the present disclosure. The method 50 of FIG. 5 is illustrated as process flow diagrams with flowchart illustrations. For purposes of simplicity, the method 50 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 50.

One or more blocks of the respective flowchart illustrations, and combinations of blocks in the block flowchart illustrations, can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, the steps/acts can be implemented by a system comprising a processor that can access the computer-executable instructions that are stored in a non-transitory memory.

The method 50 of the present disclosure may be embodied in hardware and/or in software (including firmware, resident software, micro-code, etc.). Furthermore, aspects of the present disclosure may take the form of a computer program product on a computer-usable or computer-readable storage medium having computer-usable or computer-readable program code embodied in the medium for use by or in connection with an instruction execution system. A computer-usable or computer-readable medium may be any non-transitory medium that can contain or store the program for use by or in connection with the instruction or execution of a system, apparatus, or device.

Referring to FIG. 5, an aspect of the present disclosure can include a method 50 for quantitatively measuring perfusion through a volume of interest, in accordance with an aspect of the present disclosure. For example, the volume of interest can be tissue region 16. At 52, an ultrasound signal response (e.g., ultrasound signal response received from probe 14) is received (e.g., by signal receiver 24) from a contrast agent (e.g., a contrast agent (CA) that includes microbubbles) within the volume of tissue. At 54, a probabilistic constant (e.g., $\alpha_\gamma$) related to a geometry of the volume of interest (e.g., a geometric feature X, Y and/or Z of a rectangular volume of interest) is determined (e.g., by feature selector 26). For example, the probabilistic constant can be determined based on a feature of the geometry and a scale of the volume of interest.

At 56, a ratio (e.g., R) of mean velocity (e.g., <v>) and mean path length (e.g., <L>) within the volume of interest is determined (e.g., by feature selector 26) based on the ultrasound signal response. For example, the ratio of mean velocity and mean path length can include a ratio of a first derivative of the ultrasound signal response over a first time period where the signal increases linearly and a second derivative of the ultrasound signal response over a second time period where the signal is at a steady state. At 58, the perfusion (e.g., PERF) through the volume of tissue is determined (e.g., by perfusion analyzer 28) based on the probabilistic constant and the ratio. The perfusion through the volume of tissue (<Q>) can be determined according to the following equation:

$$\langle Q \rangle = \frac{6\alpha_\gamma R}{\rho_{tissue} XY},$$

where $\alpha_\gamma$ represents the probabilistic constant, R represents the ratio of mean velocity and mean path length, $\rho_{tissue}$ represents the tissue density, and X and Y represent parameters of the feature of the geometry. For example, the perfusion through the volume of tissue can be further based on a feature of the geometry and a tissue density of the volume of interest.

Example Computer System

Figure 6:
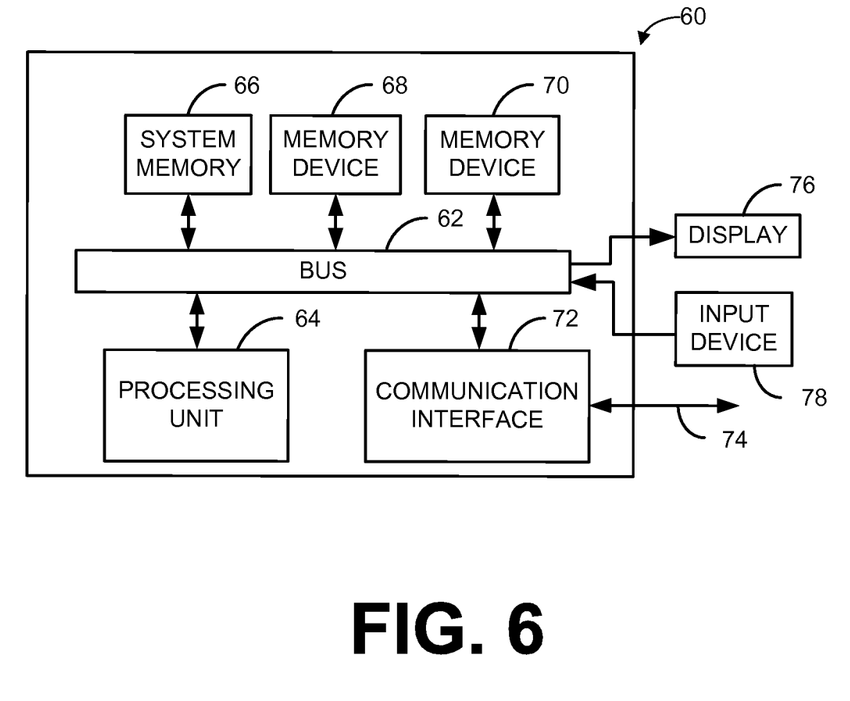
FIG. 6 is a schematic block diagram depicting an exemplary system of hardware components capable of implementing examples of the systems of FIGS. 1-2 and/or the method of FIG. 5.

FIG. 6 is a schematic block diagram illustrating a system 60 of hardware components capable of implementing examples of the systems and methods of FIGS. 1, 2, and 5. The system 60 can include various systems and subsystems, including a personal computer, a laptop computer, a workstation, a computer system, an appliance, an application-specific integrated circuit (ASIC), a server, a server blade center, a server farm, etc.

The system 60 can includes a system bus 62, a processing unit 64, a system memory 66, additional memory devices 68 and 70, a communication interface 72 (e.g., a network interface), a communication link 74, a display 76 (e.g., a video screen), and an input device 78 (e.g., a keyboard and/or a mouse). The system bus 62 can be in communication with the processing unit 64 and the system memory 66. The additional memory devices 68 and 70, such as a hard disk drive, server, stand alone database, or other non-volatile memory, can also be in communication with the system bus 62. The system bus 62 interconnects the processing unit 64, the memory devices 66, 68, and 70, the communication interface 72, the display 76, and the input device 78. In some examples, the system bus 62 also interconnects an additional port (not shown), such as a universal serial bus (USB) port.

The processing unit 64 can be a computing device that executes a set of instructions to implement the operations of examples disclosed herein. The processing unit 64 can include a processing core.

The additional memory devices 68, 70 can store data, programs, instructions, database queries in text or compiled form, and any other information that can be needed to operate a computer. The memory devices 66, 68 and 70 can be implemented as tangible computer-readable media (integrated or removable) such as a memory card, disk drive, compact disk (CD), or server accessible over a network. In certain examples, the memory devices 66, 68 and 70 can store text, images, video, and/or audio, portions of which can be available in formats comprehensible to human beings. Additionally or alternatively, the system 60 can access an external data source or query source through the communication interface 72, which can communicate with the system bus 62 and the communication link 74.

In operation, the system 60 can be used to implement one or more parts of the analysis system 18 of FIG. 2 that quantitatively measures perfusion through a volume of tissue in accordance with the present invention. Computer executable logic for implementing the identification and development system resides on one or more of the system memory 66, and the memory devices 68, 70 in accordance with certain examples. The processing unit 64 executes one or more computer executable instructions originating from the system memory 66 and the memory devices 68 and 70. The term "computer readable medium" as used herein refers to a medium that participates in providing instructions to the processing unit 64 for execution, and can, in practice, refer to multiple, operatively connected apparatuses for storing machine executable instructions.

From the above description, those skilled in the art will perceive improvements, changes and modifications. Such improvements, changes and modifications are within the skill of one in the art and are intended to be covered by the appended claims.

What is claimed is:

1. A system that measures perfusion through a volume of tissue, the system comprising:
   a non-transitory memory to store computer-executable instructions; and
   a processor that executes the computer-executable instructions to at least:
      receive an ultrasound signal response of a contrast agent within a volume of tissue as a function of time, wherein the contrast agent is infused into a patient's vasculature at a constant rate, wherein the volume of tissue comprises a and a geometry, wherein the geometry is a rectangular prism with a corresponding length, width, and height;
      determine a probabilistic constant based on the geometry of the volume of tissue;
      determine a ratio of mean velocity to mean path length based on the ultrasound signal response at a first time representing a transitory intensity and a second time corresponding to a steady state intensity;
      determine a tissue density of the volume of tissue; and
      determine a mean perfusion through the volume of tissue based on the probabilistic constant, the ratio of mean velocity to mean path length, the tissue density, the width, and the height.

2. The system of claim 1, wherein the processor executes the computer-executable instructions to determine the mean perfusion through the volume of tissue ($\langle Q \rangle$) according to the following equation:

$$\langle Q \rangle = \frac{6\alpha_\gamma R}{\rho_{tissue} XY},$$

where $\alpha_\gamma$ represents the probabilistic constant, R represents the ratio of mean velocity and mean path length, $\rho_{tissue}$ represents the tissue density, and X and Y represent the width and the height, respectively.

3. The system of claim 1, wherein the ratio of mean velocity to mean path length comprises a ratio of a first derivative of the ultrasound signal response over a first time period comprising the first time and a second derivative of the ultrasound signal response over a second time period comprising the second time.

4. The system of claim 1, wherein the processor is further configured to execute the computer-executable instructions to calibrate the mean perfusion based on intensities of borders of the volume of tissue to achieve an absolute measure of perfusion through the volume of tissue.

5. The system of claim 4, wherein the mean perfusion is calibrated by:
   identifying a voxel comprising a maximum intensity corresponding to 100% of the voxel filled with blood from the ultrasound signal response;
   identifying the voxel as within a blood vessel;
   storing the intensity value corresponding to the voxel;
   normalizing a plurality of intensity values corresponding to a plurality of voxels on the outer surface of the volume of tissue to achieve a fluid percentage within each of the plurality of voxels;
   assuming 50% of the fluid percentage flows into the volume of interest and 50% of the fluid percentage flows out of the volume of interest, such that half of the fluid flied area is used as the surface area of blood input to the volume of interest.

6. A method comprising the steps of:
   receiving, by a system comprising a processor, an ultrasound signal response of a contrast agent within a volume of tissue as a function of time, wherein the contrast agent is infused into a patient's vasculature at a constant rate, wherein the volume of tissue comprises a geometry, wherein the geometry is a rectangular prism with a corresponding length, width, and height;
   determining, by the system, a probabilistic constant based on the geometry of the volume of the tissue;
   determining, by the system, a ratio of mean velocity to mean path length based on the ultrasound signal response at a first time representing a transitory intensity and a second time representing a steady state intensity;
   determining, by the system, a tissue density of the volume of the tissue; and
   determining, by the system, a mean perfusion through the volume of tissue based on the probabilistic constant, the ratio of mean velocity to mean path length, the tissue density, the width, and the height.

7. The method of claim 6, wherein the ratio of mean velocity to mean path length comprises a ratio of a first derivative of the ultrasound signal response over a first time period comprising the first time and a second derivative of the ultrasound signal response over a second time period comprising the second time.

8. The method of claim 6, wherein the probabilistic constant is determined based on a feature of the geometry and a scale of the volume of tissue.

9. The method of claim 6, wherein the mean perfusion through the volume of tissue ($\langle Q \rangle$) is determined according to the following equation:

$$\langle Q \rangle = \frac{6\alpha_\gamma R}{\rho_{tissue} XY},$$

where $\alpha_\gamma$ represents the probabilistic constant, R represents the ratio of mean velocity to mean path length, $\rho_{tissue}$ represents the tissue density, and X and Y represent the width and the height, respectively.

10. A non-transitory computer-readable medium having stored thereon instructions that, upon execution, cause a processor of one or more computing devices to perform operations, the operations comprising:
    receiving an ultrasound signal response of a contrast agent within a volume of tissue as a function of time, wherein the contrast agent is infused into a patient's vasculature at a constant rate, wherein the volume of tissue comprises a geometry, wherein the geometry is a rectangular prism with a corresponding length, width, and height;
    determining a probabilistic constant based on to the geometry of the volume of the tissue;
    determining a ratio of mean velocity to mean path length based on the ultrasound signal response at a first time representing a transitory intensity and a second time representing a steady state intensity; and
    determining a mean perfusion through the volume of tissue based on the probabilistic constant, the ratio of mean velocity to mean path length, the tissue density, the width, and the height.

11. The computer-readable medium of claim 10, wherein the mean perfusion through the volume of tissue ($\langle Q \rangle$) is determined according to the following equation:

$$\langle Q \rangle = \frac{6\alpha_\gamma R}{\rho_{tissue} XY},$$

where $\alpha_\gamma$ represents the probabilistic constant, R represents the ratio of mean velocity to mean path length, $\rho_{tissue}$ represents the tissue density, and X and Y represent the width and the height, respectively.

12. The computer-readable medium of claim 10, further comprising calibrating the mean perfusion through the volume of tissue to obtain a value of absolute perfusion, comprising:
   identifying a voxel comprising a maximum intensity corresponding to 100% of the voxel filled with blood from the ultrasound signal response;
   identifying the voxel as within a blood vessel;
   storing the intensity value corresponding to the voxel;
   normalizing a plurality of intensity values corresponding to a plurality of voxels on the outer surface of the volume of interest to achieve a fluid percentage within each of the plurality of voxels;
   assuming 50% of the fluid percentage flows into the volume of interest and 50% of the fluid percentage flows out of the volume of interest, such that half of the fluid flied area is used as the surface area of blood input to the volume of interest.

* * * * *